United States Patent [19]
Suzuki et al.

[11] Patent Number: 5,830,488
[45] Date of Patent: Nov. 3, 1998

[54] DISINFECTANT COMPOSITION

[75] Inventors: Takashi Suzuki; Yoshio Asaka, both of Yokohama, Japan

[73] Assignee: Shiseido Co., Ltd., Tokyo, Japan

[21] Appl. No.: 309,742

[22] Filed: Sep. 21, 1994

[30] Foreign Application Priority Data

Sep. 21, 1993 [JP] Japan .................................. 5-257844

[51] Int. Cl.$^6$ .................................................. A01N 25/02
[52] U.S. Cl. ...................... 424/405; 424/401; 424/78.03; 424/78.07; 514/559
[58] Field of Search .................. 424/405, 78.07, 424/70.12, 70.27, 70.28, 78.03

[56] References Cited

U.S. PATENT DOCUMENTS 3,890,434  6/1975  Weisse et al. ...................... 424/70.2
4,642,104  2/1987  Sakamoto et al. .................. 604/264

*Primary Examiner*—Neil S. Levy
*Attorney, Agent, or Firm*—Townsend & Banta

[57] ABSTRACT

A quick drying disinfectant composition comprising 50–99 v/v% lower alcohol, a cationic disinfectant and emollient; wherein the composition further comprises cyclic or chain silicone represented by the formula:

$$[(CH_3)_2SiO]_n \text{ or } HO-[CH_3)_2SiO]_n-H$$

in which n represents an integer 2–6; and/or ester of polyhydric alcohol and fatty acid having IOB or 0.22–0.85 in which the fatty acid has straight or branched chain. The disinfectant composition of the present invention has sufficient disinfectant effect and quick drying effect without producing skin roughness or stickiness.

6 Claims, 1 Drawing Sheet

DISINFECTANT COMPOSITION

FIELD OF THE INVENTION

The present invention relates to a disinfectant composition and, more particularly, to an improvement of composition useful in hand disinfection and keeping skin from skin roughness.

BACKGROUND OF THE INVENTION

Presently, infection in a hospital has been a very serious problem, and it is very important to prevent infection in a hospital as well as medical care of a patient. It is known that infection in a hospital is caused by a medical doctor or nurse as a vector. Therefore, perfect disinfection of the hands of doctor and nurse is necessary after medical care of certain patients. For this purpose, several "quick drying disinfectant compositions" which include ethanol as a main ingredient have been developed and commercialized.

Examples of the quick drying disinfectant compositions are ethanol solutions including benzalkonium chloride or chlorhexidine gluconate, which are prepared by adding 0.1 to 4% of benzalkonium chloride or chlorhexidine gluconate to ethanol solution for disinfection. However, if a person uses a ethanol solution which includes 76.9 to 81.4 v/v% of ethanol every time when they care for a patient, skin roughness may be caused. Therefore, although disinfection of the hands is necessary after rendering care, there are many cases in which it is not enough to disinfect the hands. Furthermore, micro-organisms can easily contaminate the rough skin of hands, and secondary infection may be caused.

On the other hand, it can be considered to add emollient ingredients to a disinfectant composition which includes ethanol as a main ingredient (JAPANESE PATENT LAID OPEN NO.57-165305, 1-132515, JAPANESE PATENT PUBLISHED NO.4-33226, 5-63446). However, emollient ingredients makes the hands sticky and have a bad influence upon the disinfecting effect of a disinfectant, such as benzalkonium chloride or chlorhexidine gluconate.

As described above, there is no disinfectant composition which can be used often and has a sufficiently enough disinfecting and quick drying effects without resulting in stickiness and skin roughness.

SUMMARY OF THE INVENTION

It is an object of the present invention to eliminate the problems of the prior art and to provide a disinfectant composition which has a sufficient disinfectant effect and quick drying effect without skin roughness or stickiness.

As a result of studies undertaken by the present inventors so as to achieve these goals, it has been found that a mixture of emollient ingredient, polar oil and cyclic or chain silicone can achieve the objective. On the basis of these findings, the present invention has been achieved.

In the first aspect of the present invention, there is provided a disinfectant composition comprising; lower alcohol, a cationic disinfectant, an emollient ingredient, wherein the composition further comprising;
cyclic or chain silicone represented by the formula 1;

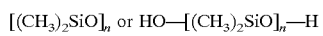

of which n is an integer 2–6; and /or
ester of polyhydric alcohol and fatty acid having IOB from 0.22 to 0.85. The fatty acid may be a straight chain or branched chain.

The term "disinfectant composition" is used herein to encompass a disinfectant composition not only for the hands and finger but also for the skin of a patient and for a medical device.

The cationic disinfectant of the present invention may comprise benzalkonium chloride having carbon atoms from 8 to 18, benzethonium chloride, chlorhexidine gluconate, alkyl isoquinolinium bromide, alkyl trimethylammonium chloride having carbon atoms from 8 to 24, N-cocoil-L-arginine ethyl ester-DL pyrolidone carbonate represented by the formula 2;

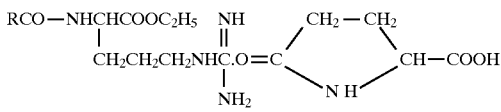

wherein RCO— is a residue of coconut fatty acid.

The cationic disinfectant comprises an ordinary content of disinfectant such as 0.02–4 w/v% and, more preferably 0.05–0.5 w/v% in accordance with solubility of the disinfectant.

The lower alcohol of the present invention may preferably comprise ethanol or isopropyl alcohol. The amount of ethyl alcohol is preferably in the range 76.9–81.4 v/v% in accordance with disinfection effect. However, the amount of ethanol may be in the range 50–99 v/v% of ethanol solution. Further, it is particularly effective to add 0.5–5.0 v/v% of isopropyl alcohol to the composition in disinfection effect.

The emollient of the present invention may preferably comprise polyhydric alcohol such as polyethylene glycol, glycerin, diglycerin, propylene glycol, butylene glycol, erythritol, dipropylene glycol, sorbitol, maltitol; pyrrolidone carbonate; sodium lactate and urea. Particularly preferred emollients is one or more emollients selected from a group consisting of polyethylene glycol, glycerin, propylene glycol, butylene glycol, erythritol, dipropylene glycol and sorbitol. The amount of emollient may be in the range 0.1–3.0 w/w% and, more preferably in the range 0.2–1.5 w/w%. In the case where the content of the emollient is less than 0.1 wt %, it may not be enough to preventing the effect of skin roughness. Also, in the case where the content of the emollient is over 3.0 w/w%, it may not be possible to prevent stickiness.

The cyclic or chain silicone and the ester of polyhydric alcohol and fatty acid having IOB of 0.22–0.85 are added to prevent stickiness when the emollient is added more than certain amount and volatilization of water from skin. It has been found that the cyclic or chain silicone and the polar oil having IOB in the range 0.22–0.85 are particularly effective to prevent stickiness and roughness of the skin.

The ester of polyhydric alcohol and the fatty acid of the disinfectant composition of the present invention may comprise esters of propylene glycol and fatty acid having carbon atoms of 9–15, diester of glycerin and fatty acid having carbon atoms of 15–27, triester of glycerin and fatty acid having carbon atoms of 21–39, sorbitan fatty acid ester having carbon atoms of 12–18, triester of penta erythritol and fatty acid having carbon atoms of 23–41, tetraester of penta erythritol and fatty acid having carbon atoms of 29–53. These may be a mixture.

In a preferred composition of the present invention, the polyhydric alcohol is triester of glycerin and fatty acid (triglyceride) having carbon atoms from 21 to 39. The triglyceride may be selected from triglyceride of medium chain fatty acid (available commercially for example under the trade name Panasate 875 of NIHON YUSHI CORP. and Tristar-S-810 of NIHON CHEMICALS CORP.); plant oils such as olive oil, soybean oil, sesame oil, safflower oil and corn oil; synthesized oil such as glyceryl tri 2-ethylhexanoate (available commercially for example under the trade name RA-G-308) The particularly effective trygryceride is RA-G-308.

The amount of ester of polyhydric alcohol and fatty acid having IOB of 0.22–0.85 is preferably in the range 0.2–5.0 wt % and, more preferably in the range from 0.5 to 3.0 wt %. In the case where the content is less than 0.2 wt %, it is difficult to eliminate stickiness. In the case where the content is over 5.0 wt %, stability of the composition is not good and a greasy feeling occurs.

The cyclic or chain silicone of the disinfectant composition of the present invention is represented by the formula 1 and effectively suppresses stickiness after drying the composition. The silicone easily volatilizes from the skin, so it is particularly effective to improve usability comparing the polar oil. The amount of the silicone is preferably in the range from 0.1 to 2.0 wt %. In the case where the content is less than 0.1 wt %, it may not be enough to eliminate stickiness and the where content is over 2.0 wt %, sliminess of the silicone or decreased stability may occur. In the case where n is over integer 7, solubility in ethanol for disinfectant is not good, and where n is less than integer 1, the suppressing effect of stickiness of glycerin is not enough.

The total amount of the cyclic or chain silicone and/or ester of polyhydric alcohol and fatty acid is preferably in the range from 0.1 to 5.0 wt % in stability and usability. The ratio of the amount of emollients and total amount of the silicone and/or the ester of polyhydric alcohol and fatty acid is preferably 1:0.5 to 1:2.0 by weight in useability (stickiness).

The compositions of the present invention may additionally comprise other components which will be well known to those skilled in the art for example drugs such as glycyrrhizic acid and its derivatives, vitamin E, vitamin E acetate and vitamin $B_6$; water soluble polymers such as xanthan gum, dextrin, hydroxy ethyl cellulose, hydroxy methyl cellulose, methyl cellulose, carageenan and carboxy methyl cellulose.

EXAMPLES

Figure 1:
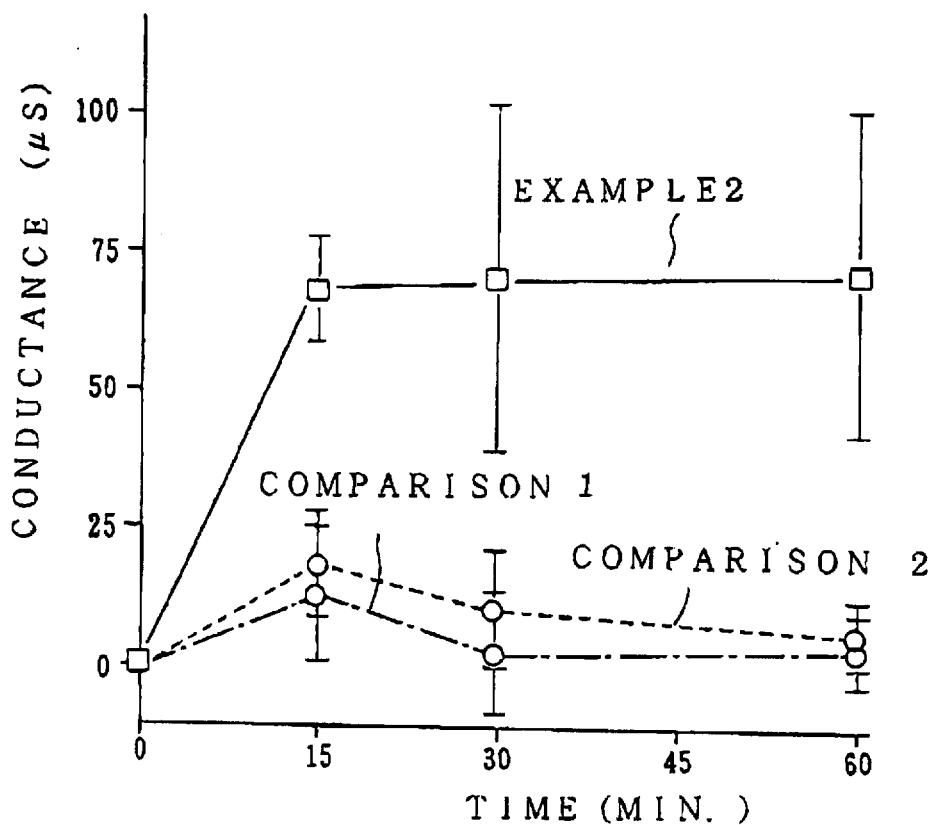
FIG. 1 is an explanatory view which shows the change of conductance of skin with time when the disinfectant composition of the present invention is applied on the hand, compared to when a disinfectant composition of the prior art is applied

A preferred embodiment of the present invention will be explained hereinunder. The content is expressed by weight %.

Examples 1 to 5, Comparison 1 to 3

As main ingredients of emollients, ester of polyhydric alcohol and fatty acid and cyclic or chain silicone which could be dissolved in ethanol solution for disinfectant, glycerin, triglyceride (triglyceryl tri(2-ethylhexanoate)), cyclic silicone (decamethyl cyclo tetra siloxane) and chain silicone (methyl poly siloxane: 2cs, n=3) were selected and added to ethanol solution for disinfectant including 0.2% of benzalkonium chloride and 0.02% of CAE. The contents of these ingredients were changed according to each sample and the efficacy of the compositions were measured in user tests. The tested items were: preventing effect of skin roughness, sliminess at applying the compositions, stickiness after drying, and emollient effect after drying. The users consisted of 20 persons and the results were given as an average of the index the users evaluated.

Standard

3: excellent
2: good
1: average
0: not good

The results are given below.

TABLE 1

|  | COMPARISON | | | EXAMPLE | |
| --- | --- | --- | --- | --- | --- |
|  | 1 | 2 | 3 | 1 | 2 |
| Ethanol | 75.0 | 75.0 | 75.0 | 75.0 | 75.0 |
| Chlorhexidine gluconate | — | — | — | — | — |
| Benzalkonium chloride | 0.2 | 0.2 | 0.2 | 0.2 | 0.2 |
| CAE | 0.02 | 0.02 | 0.02 | 0.02 | 0.02 |
| Glycerin | — | — | 1.0 | 1.0 | 1.0 |
| Chain silicone | — | — | — | — | — |
| Cyclic silicone | — | — | — | — | 0.2 |
| Triglyceride | — | 0.5 | — | 0.5 | 0.3 |
| Lactic acid | — | — | — | — | — |
| Purified water | 24.78 | 24.28 | 23.78 | 23.28 | 23.28 |
| Sliminess | 1.5 | 1.2 | 1.6 | 1.1 | 1.7 |
| Stickiness | 1.9 | 1.7 | 0.8 | 1.6 | 1.9 |
| Emollient effect | 0.7 | 1.0 | 1.0 | 1.8 | 2.3 |
| Preventing effect on skin roughness | 0.7 | 1.6 | 1.4 | 2.4 | 2.4 |

TABLE 2

|  | EXAMPLE | | | | |
| --- | --- | --- | --- | --- | --- |
|  | 3 | 4 | 5 | 6 | 7 |
| Ethanol | 75.0 | 75.0 | 75.0 | 75.0 | 75.0 |
| Chlorhexidine gluconate | — | — | — | — | 0.2 |
| Benzalkonium chloride | 0.2 | 0.2 | 0.2 | 0.2 | — |
| CAE | 0.02 | 0.02 | 0.02 | 0.02 | 0.02 |
| Glycerin | 2.0 | 1.0 | 2.0 | 1.0 | 1.0 |
| Chain silicone | — | — | — | — | 0.2 |
| Cyclic silicone | 0.2 | 0.5 | 2.0 | 0.2 | — |
| Triglyceride | 0.3 | 0.3 | 3.0 | — | 0.3 |
| Lactic acid | — | — | — | — | 0.05 |
| Purified water | 22.28 | 22.98 | 17.78 | 23.58 | 23.23 |
| Sliminess | 1.7 | 1.2 | 0.6 | 1.7 | 1.7 |
| Stickiness | 1.4 | 1.8 | 0.7 | 0.8 | 1.9 |
| Emollient effect | 2.4 | 2.0 | 2.0 | 1.7 | 2.3 |
| Prevention effect on skin roughness | 2.5 | 2.5 | 2.7 | 2.2 | 2.5 |

Changes of conductance (gs) of skin with time (min.) were tested with respect to Example 2, and Comparison 1 and 2 which were similar to commercially available compositions. 100 ml of each samples was applied on 25 cm$^2$ of forearm skin under 25° C. and 50%-humidity. The conductance was measured using Skicon 20D (commercially available from Nihon IBS corp.). The results are given in FIG. 1. As is well known, the conductance of skin relates to a content of water. FIG. 1 shows that the skin on which the disinfectant composition of the present invention was applied included greater moisture than that of the comparisons which were applied and, maintained the moisture after the application.

Example 8

1.0 w/v% of sorbitol, 0.3 w/v% of triglyceride (triglyceryl tri2-ethylhexanoate) and 0.2 w/v% of cyclic silicone (decamethyl cyclo tetra siloxane) are selected as main ingredients of emollients, the ester of polyhydric alcohol and fatty acid and/or cyclic or chain silicone; and 0.02 w/v% of CAE as a disinfectant were added to ethanol for disinfectant including 0.25% of chlorhexidine gluconate. The composition so obtained was tested for the disinfection effect on the skin.

The test was conducted according to the following method.

*Staphylococcus aureus* FDA 209P was cultured in a liquid bouillon culture medium for 20 hours at 37° C. The medium was diluted 2000 times by adding sterilized saline. 0.1 ml of the diluted medium (including about $10^5$ cfu of the staphylococcus) was poured in a glass column (3 cm-diameter) of which the bottom was contacted with skin. The diluted medium was applied using a sterilized glass stick and naturally dried. After drying, 2 ml of the disinfectant composition was poured in the column and uniformly applied using a sterilized glass stick. After 1 min., 0.1 ml of the applied composition was collected by a pipette, and added to 100 ml of SCDLP culture medium. The SCDLP culture medium was incubated for 48 hours at 37° C. The medium so obtained was applied on a Forgel-Jonson agar culture medium. After culture, existence of the *staphylococcus aureus* was tested. As a result, although *staphylococcus albus* and *apospre bacillus* could be observed, the *staphylococcus aureus* could not be observed. The result shows that the disinfectant composition has excellent disinfection effect. The SCDLP culture medium which was used for the above application included lecithin and Polysorbate 80 which deactivated chlorhexidine gluconate. Further, the SCDLP culture medium was diluted to an amount of 100 ml to prevent inhibiting of development of micro-organisms.

Example 9

1.0 w/v% of glycerin, 0.3 w/v% of triglyceride (triglyceryl tri(2-ethylhexanoate)) and 0.2 w/v% of cyclic silicone (decamethyl cyclo tetra siloxane) are selected as main ingredients of emollients, the ester of polyhydric alcohol and fatty acid and/or cyclic or chain silicone, and 0.02 w/v% of CAE as a disinfectant were added to ethanol for disinfectant including 0.1% of benzalkanium chloride. The composition so obtained was tested prevention of the effect of stickiness and disinfection effect on the skin.

The test was conducted according to the following method.

*Staphylococcus aureus* FDA 209P was cultured in a liquid bouillon culture medium for 20 hours at 37° C. The medium was diluted 2000 times by adding sterilized saline. *Pseudomonas aeruginosa* was cultured according to same method. 1 ml of each diluted medium (including about $10^6$ micro-organisms) was applied on a hand and naturally dried. After drying, 2 ml of the disinfectant composition was applied on the hand. After drying, a sterilized rubber-glove was put on the hand, 50 ml of LP-dilution solution (Daigo corp.) (37° C.) was poured in the glove and rubbed into the hand for 1 minute. The solution was collected and existence of microorganism was tested using a SCDLP culture medium and a LP-diluted solution. A blank test was conducted according to the above method same way but using 50 ml of sterilized saline instead of the disinfectant composition. Stickiness was also tested by applying 2 ml of the composition on a hand.

Each of the user test was conducted for 5 persons (panels). The results were given in Table 3.

TABLE 3

| PANEL | A | B | C | D | E |
|---|---|---|---|---|---|
| Blank test: | | | | | |
| S. aureus | $1.1 \times 10^5$ | $1.5 \times 10^6$ | $1.3 \times 10^5$ | $1.1 \times 10^6$ | $1.3 \times 10^5$ |
| P. aeruginosa | $2.4 \times 10^2$ | $1.8 \times 10^8$ | $4.7 \times 10$ | $2.9 \times 10^2$ | $1.6 \times 10^2$ |
| After disinfection: | | | | | |
| S. aureus | <5 | <5 | <5 | <5 | <5 |
| S. aeruginosa | <5 | <5 | <5 | <5 | <5 |
| Stickiness after disinfection | none | none | none | none | none |

IN Table 3, "<5" indicates that no microorganism can be observed.

Example 10

1.5 w/v% of glycerin, 0.35 w/v% of triglyceride (triglyceryl tri(2-ethylhexanoate)) and 0.3 w/v% of cyclic silicone (decamethyl cyclo tetra siloxane) are selected as main ingredients of emollients, the ester of polyhydric alcohol and fatty acid and/or cyclic or chain silicone and added to ethanol for disinfectant including 0.2% of chlorhexidine gluconate. The composition so obtained was tested for the preventing effect of roughness skin under repeated use.

The test was conducted according to the following method.

2 ml of the prepared disinfectant composition was applied on a hand and dried. The same procedure was repeated 12 times at intervals of 10 minutes. 10 persons conducted the test and the test was repeated for 5 days. The evaluation of skin roughness was evalnated by themselves. The results of each persons are given in TABLE 4. The evaluation method is the same as Example 1.

TABLE 4

| PANEL | A | B | C | D | E | F | G | H | I | J |
|---|---|---|---|---|---|---|---|---|---|---|
| SCORE | 2 | 2 | 3 | 2 | 3 | 2 | 3 | 1 | 3 | 3 |

Comparison 4

A disinfectant composition was prepared according to the following formula. In the formula, silicone was not cyclic or chain silicone of the present invention.

| | |
|---|---|
| Ethanol | 75.0 wt % |
| Benzalkonium chloride | 0.2 |
| CAE | 0.02 |
| 1,3-butylene glycol | 1.0 |
| Metylphenyl polysiloxane | 0.2 |
| Isopropyl myristate (IPM) | 0.3 |
| Purified water | 23.28 |

The obtained composition has not good usability. The usability depends on the silicone component and IPM so that a feeling of film remains on the hand and is too smooth because the methylphenyl polysiloxane is not a volatile compound.

As explained above, the disinfectant composition of the present invention has enough disinfection effect without skin roughness or stickiness. Therefore, it is possible to use this composition safely and very frequently for a medical worker and nurse.

What is claimed is:

1. A quick drying disinfectant composition consisting essentially of 50–99 v/v% of ethanol or isopropanol, a cationic disinfectant, an emollient, and a cyclic or chain volatile liquid silicone soluble in ethanol represented by the formula:

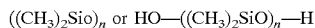

$((CH_3)_2SiO)_n$ or $HO-((CH_3)_2SiO)_n-H$ in which n represents an integer of 2–6, and wherein the ratio of the amount of emollient and the total amount of cyclic or chain silicone is 1:0.1 to 1:2.0 by weight and the cyclic or chain volatile liquid silicone is 0.1 to 2.0 wt. % of the composition, and the content of said cationic disinfectant is 0.05–0.5 w/v%.

2. A disinfectant composition according to claim 1, wherein the emollient is selected from the group consisting of polyethylene glycol, glycerin, diglycerin, propylene glycol, butylene glycol, erythritol, dipropylene glycol and sorbitol.

3. A quick drying disinfectant composition consisting essentially of 50–99 v/v% of ethanol or isopropanol, a cationic disinfectant, an emollient, and a cyclic or chain volatile liquid silicone soluble in ethanol represented by the formula:

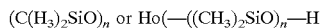

$(C(H_3)_2SiO)_n$ or $Ho(-((CH_3)_2SiO)_n-H$ in which n represents an integer of 2–6, wherein the ratio of the amount of emollient and the total amount of cyclic or chain volatile liquid silicone is 1:0.1 to 1:2.0 by weight, the cyclic or chain volatile liquid silicone is 0.1 to 2.0 wt. % of the composition, and the content of said cationic disinfectant is 0.02–4 w/v%.

4. A disinfectant composition according to claim 3, wherein the emollient is selected from the group consisting of polyethylene glycol, glycerin, diglycerin, propylene glycol, butylene glycol, erythritol, dipropylene glycol and sorbitol.

5. A disinfectant composition according to claim 1, wherein said cationic disinfectant is selected from the group consisting of benzalkonium chloride having from 8–18 carbon atoms, benzethonium chloride, chlorhexidine gluconate, alkyl isoquinolinium bromide, alkyl trimethylammonium chloride having from 8–24 carbon atoms, N-cocoil-L-arginine ethyl ester-DL pyrolidone carbonate represented by the following formula:

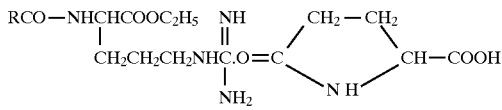

wherein RCO— is a residue of coconut fatty acid.

6. A disinfectant composition according to claim 3, wherein said cationic disinfectant is selected from the group consisting of benzalkonium chloride having from 8–18 carbon atoms, benzethonium chloride, chlorhexidine gluconate, alkyl isoquinolinium bromide, alkyl trimethylammonium chloride having from 8–24 carbon atoms, N-cocoil-L-arginine ethyl ester-DL pyrolidone carbonate represented by the following formula:

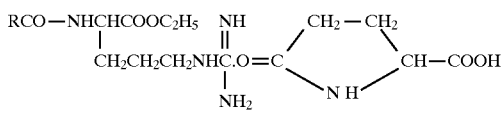

wherein RCO— is a residue of coconut fatty acid.

* * * * *